United States Patent [19]

Dokus et al.

[11] 4,147,990
[45] Apr. 3, 1979

[54] FAST-RECOVERY CIRCUIT

[75] Inventors: Edwin A. Dokus, Winchester; Thomas K. Naylor, Belmont, both of Mass.

[73] Assignee: American Optical Corporation, Southbridge, Mass.

[21] Appl. No.: 884,322

[22] Filed: Mar. 7, 1978

[51] Int. Cl.² ............................................. H03F 21/00
[52] U.S. Cl. .................................... 330/11; 328/171; 330/85; 330/110
[58] Field of Search ..................... 330/9, 11, 85, 110, 330/290; 328/132, 171, 175; 128/2.06 B

[56] References Cited

U.S. PATENT DOCUMENTS 3,611,174  10/1971  Day ................................. 330/110 X

Primary Examiner—James B. Mullins
Attorney, Agent, or Firm—Jeremiah J. Duggan; Stephen A. Schneeberger; Howard R. Berkenstock, Jr.

[57] ABSTRACT

An improved fast-recovery circuit for ECG amplifiers and the like. The fast-recovery circuit includes threshold responsive circuitry connected in parallel with part of the resistance associated with the integrator in a feedback circuit of the amplifier. The threshold responsive circuitry operates to increase feedback frequency response of the integrator when the normally very low frequency output signal of the amplifier exceeds a certain threshold. The improved circuit prevents the threshold circuitry from responding to pulses or excursions in the output signal of a relatively higher frequency content and which exceed the amplitude threshold for less than a predetermined interval, as for instance caused by pacer spikes, large QRS complexes and the like. Preferably, the improved threshold responsive means comprises transistor means connected across the integrator's resistance and having capacitance means across the base-emitter circuit thereof for inhibiting response to certain short duration signals.

8 Claims, 2 Drawing Figures

FAST-RECOVERY CIRCUIT

BACKGROUND OF THE INVENTION

This invention relates generally to amplifier circuitry and more particularly to base line restoration circuitry for amplifiers. More particularly still, the invention relates to an improved fast-recovery circuit for amplifiers.

In a variety of applications employing amplifiers, the input signal, and more importantly the output signal, may develop some degree of DC or low frequency offset which may tend to distort the informational content of any desired signal super-imposed thereon and/or may further cause a display thereof to be driven off scale. Therefore it is desirable to remove or minimize this offset such that the output signal reflects only a nonoffset representation of the desired signal applied to the input. Various offset correction or base line restoration circuits have been developed for cancelling or substantially eliminating offset appearing in the output signal. One technique used to accomplish this end is the employment of a negative feedback loop connected from the output of the amplifier through an integrator to the amplifier input. The integrator is substantially nonresponsive to signals having frequencies much above DC and accordingly only provides feedback of a correction or cancelling signal corresponding with the DC or very low frequency offset value. This technique minimizes attenuation of the desired signal.

In addition to very low frequency or DC offset values, other large signals such as pacemaker and/or defibrillation pulses appearing at the input of an ECG amplifier may cause an overload condition which so affects the RC integrating circuit of the feedback loop that restoration of the normal output base line may be delayed for a considerable time. During that time, a display provided by the amplifier output may be entirely off scale. To at least partially remedy this condition, speed-up or fast-recovery circuits have been used in conjunction with the integrator to change its time constant whenever the amplifier output exceeds some threshold value. This enables the output to return to operation within its voltage limits in a more rapid manner. Most of these fast-recovery circuits have employed a string of diodes connected in parallel with all or a portion of the resistance in the integrator's RC network. The accumulated voltage drops of the several diodes were utilized to define the threshold above which amplifier output levels would cause conduction through the diodes and bypass the resistance. The reduced RC time constant enables the integrator to respond more rapidly to any overload, such as result from sudden changes in electrolytic cell voltage of the patient monitored, from pacemakers, and defibrillators, to return the signal to the amplifier's linear output range. A drawback to this technique does exist, however, and has been termed by some as the "bump-bump" phenomenon. More specifically, when a high-voltage pulse or excursion does occur and the diodes conduct, a relatively large charge is rapidly applied to a capacitance connected to the integrator. Then, when the high-voltage pulse has passed and the diodes cease conducting, that large charge remains on the capacitance and the relatively large resistance of the RC time constant has similarly been returned to the circuit. This results in the base line of the amplifier's output being offset in the opposite direction of the pulse excursion, which offset is only slowly nullified because the integrator has now returned to its DC or low frequency response mode.

Accordingly, it is a principal object of the present invention to provide an improved fast-recovery circuit for an amplifier, such as used in ECG signal processing. Included within this object is the provision of a fast-recovery circuit which rapidly returns the amplifier output to operation within its voltage limits whenever excessively large amplitude very low frequency signals occur, yet substantially eliminates any resulting base line offset as the result of high amplitude, relatively higher frequency or short interval signals such as pacer pulses, large QRS complexes and the like.

SUMMARY OF THE INVENTION

In accordance with the invention, there is provided for electrocardiographic (ECG) amplifiers and the like an improved fast-recovery circuit. The fast-recovery circuit is connected in the amplifier output to a feedback circuit in turn connected to the amplifier input. The feedback circuit includes an integrator having resistance and capacitance associated therewith for normally supplying low frequency feedback to the amplifier input to cancel low frequency offset appearing thereat. The fast-recovery circuit includes threshold responsive circuit connected in parallel with at least a substantial portion of the resistance associated with the integrator. The threshold circuitry normally has a relatively high impedance which changes to a low impedance state when the very low frequency amplifier output signal exceeds a characteristic amplitude threshold level, thereby to increase the feedback frequency response of the integrator. The improved fast-recovery circuit additionally provides circuitry for preventing the threshold circuitry from responding to pulses or excursions in the amplifier output signal which are of a relatively higher frequency content and exceed the amplitude threshold for less than a predetermined interval. Specifically, the fast-recovery circuit is prevented from responding to high-voltage excursions such as pacer spikes, large QRS complexes, and the like which exceed the threshold for relatively short intervals, i.e., less than about 2–30 milliseconds.

In a preferred embodiment, the threshold circuitry of the improved fast-recovery circuit utilizes a transistor and a voltage divider to bypass the integrator resistance when the output exceeds some predetermined threshold level. The transistor is connected in grounded-base configuration with the collector-emitter connected to shunt the integrator's resistance and to receive a bias voltage from a voltage divider. By connecting a capacitor across the base-emitter junction of the transistor, high-voltage but short-duration pulses, such as pacer spikes, have substantially no effect on the bias voltage and are inoperative to cause the transistor to conduct. Only those voltages of relatively long duration which exceed the established threshold level are capable of adjusting the bias sufficiently to cause the transistor to conduct. A diode is connected in the voltage divider network to compensate for the transistor's base-emitter temperature dependence.

DESCRIPTION OF A PREFERRED EMBODIMENT

Figure 1:
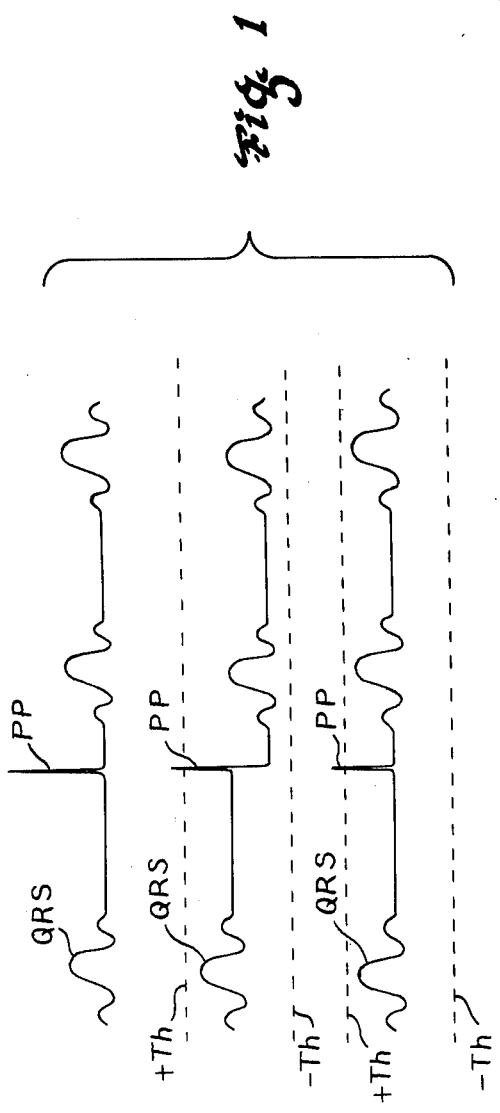
FIG. 1 illustrates three separate traces of an ECG waveform including a pacer pulse, the uppermost trace being the actually-detected electrical signal, the middle trace being at the output of an amplifier utilizing a prior art fast-recovery circuit, and the lowermost trace being at the output of an amplifier utilizing the improved fast-recovery circuit of the invention.
Figure 2:
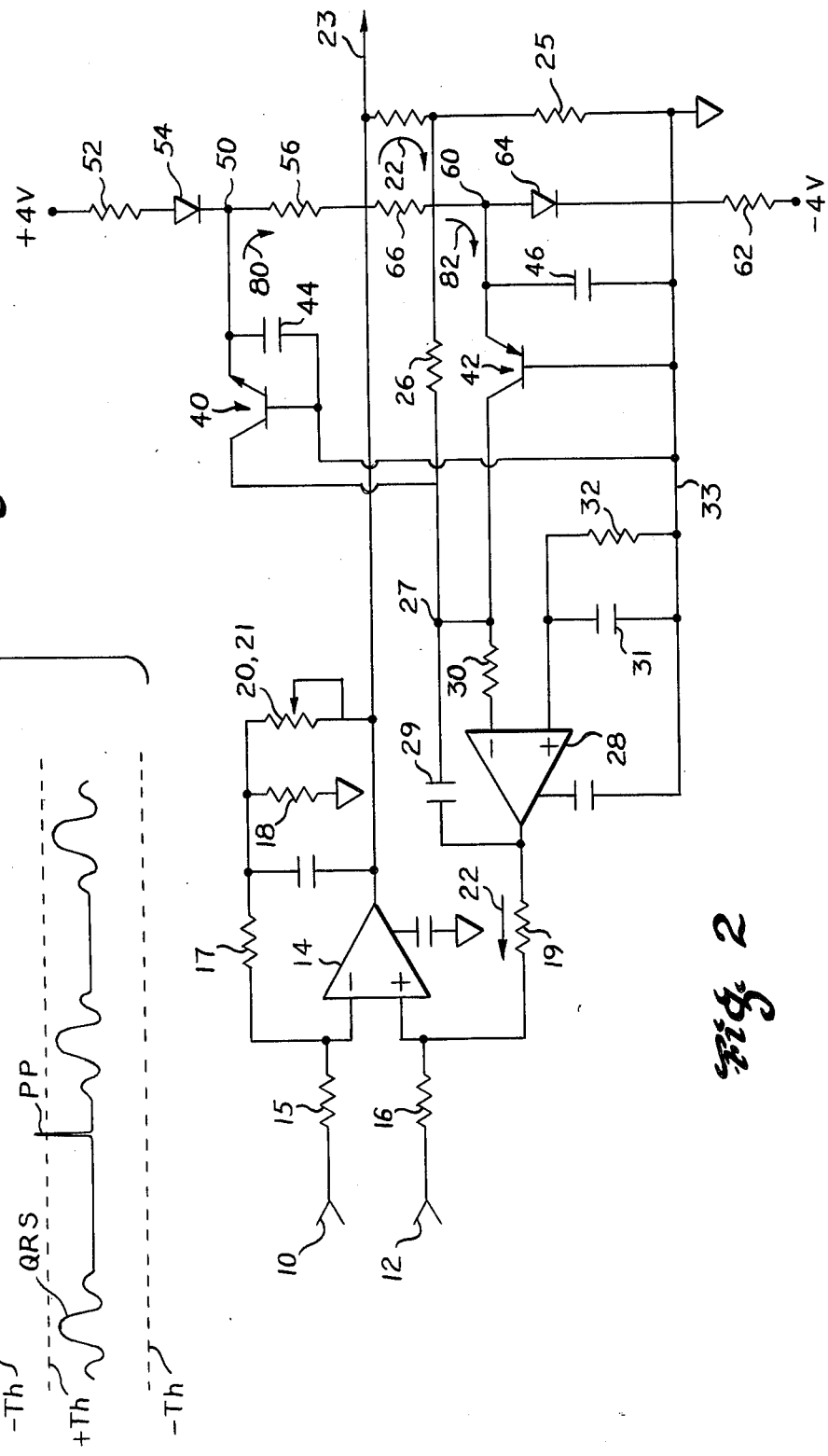
FIG. 2 is a detailed schematical diagram of an ECG amplifier employing the improved fast-recovery circuit of the invention.

Referring to FIG. 2, there is illustrated at least a portion of an ECG amplifier incorporating an improved fast-recovery circuit in accordance with the present invention. Inputs 10 and 12 to that circuitry may typically comprise the outputs of a guarded-input differential amplifier or preamplifier of the type disclosed in U.S. application Ser. No. 884,326 filed Mar. 7, 1978 by Thomas K. Naylor for Input Overload Protection Circuit. The differential voltage appearing between inputs 10, 12 typically is of the form illustrated in the uppermost trace of FIG. 1 and includes a succession of PQRST complexes (only the QRS portion being identified) and a pacer pulse PP. The differential voltage between inputs 10, 12 are applied to the respective inputs of a differential amplifier 14 having a single-ended output. The voltage of input 10 is extended through resistor 15, comprising one arm of a bridge, to the inverting input of the operational amplifier forming differential amplifier 14. Similarly, the signal voltage on input 12 is extended through resistor 16, forming another arm of the bridge, to the noninverting input of amplifier 14. Resistors 15 and 16 form two arms of a four-arm bridge having amplifier 14 connected therebetween. The third arm of the bridge includes resistors 17 and 18, and the final arm of the bridge includes resistor 19. The values of resistors 15, 16, 19 and the combined resistances of resistors 17, 18 are substantially equal. This bridge arrangement ensures that common mode voltages appearing at the input are substantially rejected and that the single-ended output of amplifier 14 reflects only the differential voltage.

One end of resistor 18 is connected to ground, the other end being connected to resistor 17 which is in turn connected to the inverting input of amplifier 14. A variable resistance comprised of resistors 20 and 21 is connected between the output of amplifier 14 and the junction of resistor 18 with resistor 17. Resistors 18 and 20 are scaled to provide a gain of about fifty to amplifier 14.

The bridge arm containing resistor 19 as connected from the output of amplifier 14 to its noninverting input is additionally utilized as a feedback loop having an integrator for base line restoration. More specifically, the feedback loop is normally represented by the arrows 22 and includes the path from the output 23 of amplifier 14, through resistor 24 of an attenuator which also includes resistor 25, through the large (12 megohm) integrator resistor 26 to a summing junction 27, from summing junction 27 through the remainder of the integrator comprised of operational amplifier 28 and capacitor 29, thence through bridge resistor 19 to the noninverting input of amplifier 14. Because the integrator is intended to compensate for DC or very low frequency offset, i.e., below about 5 Hz, its RC time constant is necessarily quite large. Accordingly, capacitor 29 is also of relatively large value, for example, 4 microfarads. Thus the RC time constant of resistor 26 and capacitor 29 is about 50 seconds. This relatively large time constant is required because of the loop gain of amplifier 14. In fact, an even larger RC time constant would be required were it not for the fact that the value of the output signal extended to resistor 26 is scaled down by the attenuator or voltage divider 24, 25. A small input resistor 30 is connected from summing junction 27 to the inverting input of operational amplifier 28 to protect the amplifier. Integrating capacitor 29 is connected from summing junction to the output of amplifier 28. A bias-current offset-balancing network comprised of parallel connected capacitor 31 and resistor 32 extends from the grounded reference conductor 33 to the noninverting input of amplifier 28.

In the event a DC or very low frequency offset appears in the output signal from amplifier 14, that offset will gradually be reflected, in inverted form, at the output of the integrator which is subsequently applied to the noninverting input of amplifier 14. In this way, any offset tends to be cancelled.

However, in the event of large amplitude differential signals suddenly appearing at inputs 10, 12 the output of amplifier 14 would normally be driven to its limit, in this instance about 3 volts, and remain clamped there so long as the limit was exceeded. This, of course, drives the output of any display device off scale and/or clips that portion of the signal exceeding the amplifier's limits. However, due to the large magnitude of this apparent offset and the relatively slow response time of the integrator, the output of amplifier 23 may remain at its limit for an extremely long time while the integrator slowly corrects for the offset. To prevent this, prior art fast-recovery circuits have employed threshold-actuated circuitry such as a series string of diodes connected between the amplifier output and the point equivalent to summing junction 27. The conduction (thresholds) of the several diodes in series established the threshold above which the amplifier output signal would initiate conduction therethrough. The conduction path through the diodes was of substantially lower impedance than that through the input resistor corresponding to resistor 26 substantially in parallel therewith, and thus the time constant for the integrator was substantially reduced and accordingly its response rate was significantly accelerated. In that way the integrator was able to more rapidly correct for large amplitude offsets appearing at the output of the amplifier to return the base line to or nearly to its zero offset position. However, in the instance of a high amplitude signal of relatively higher frequency or shorter interval supplied to the inputs 10, 12, such as a pacer pulse PP, or even a large QRS complex, a capacitor would be charged (or discharged) relatively quickly to relatively rapidly generate an offset-cancelling input to amplifier 14. However, because this excursion terminates shortly thereafter, i.e., about 2 milliseconds for a pacer pulse, and the diodes return to nonconduction thereby establishing the large RC time constant circuit once again, the offset-correction to the integrator from this capacitor persists for a particularly long time during which there may no longer be an offset appearing at the output of amplifier 14. This situation is illustrated in the middle trace of FIG. 1 in which the base line is undesirably shifted in the negative direction at the conclusion of a pacer pulse PP and only slowly recovers thereafter.

The series-diode networks of the prior art fast-recovery circuits additionally possessed thresholds which were temperature-sensitive and somewhat fuzzy or indistinct. This tended to cause some distortion below the overload point inasmuch as the threshold was neither well-defined nor repeatable under varying temperature conditions.

In accordance with the present invention, as illustrated in FIG. 2, the diode fast-recovery circuits are replaced by active elements such as complementary transistors 40 and 42 which are connected in a temperature-compensating threshold or bias-establishing network. More importantly, additional circuit elements such as capacitors 44 and 46 associated with transistors 40 and 42 respectively serve to prevent conventional operation of the fast-recovery circuitry in the event the threshold-exceeding signal is of higher frequency than about 5 Hz and thus is only of relatively short duration, i.e., less than about 2-30 milliseconds. It will be appreciated that the "tip" of a large QRS complex which exceeds the threshold usually has a frequency content somewhat above 5 Hz and may exceed the threshold for an interval less than about 30 milliseconds. Both the NPN transistor 40 and the PNP transistor 42 are connected in the grounded-base configuration with their respective bases connected to conductor 33. The collectors of transistors 40, 42 are connected to summing junction 27, and their respective emitters are connected to separate but symmetrical biasing circuits.

The emitter of transistor 40 is connected to junction or tap 50 of a voltage divider or biasing network which extends from a +4 volt supply to the amplifier output conductor 23 and includes, in series, resistor 52, diode 54, junction 50 and resistor 56 respectively. Similarly, the emitter of transistor 42 is connected to a junction 60 in a voltage divider or biasing network extending between a −4 volt supply and amplifier output conductor 23 and including in series resistor 62, diode 64, junction 60 and resistor 66 respectively. The corresponding elements in the biasing networks for both transistors 40 and 42 are preferably of identical value, with the respective diodes 54 and 64 being poled to conduct toward and away from conductor 23 respectively. The voltage drop across diodes 54, 64 is typically one-half volt each, with resistors 52, 62 typically having values of 18.2 K ohm each and resistors 56, 62 typically having resistances of 10 K ohm each. These values are selected such that the quiescent potentials (i.e., about +1 V., −1 V. respectively) applied to the respective junctions 50, 60 strongly back-bias transistors 40, 42 to maintain them in their nonconductive states.

The turn-on bias voltage for transistor 40 is about −0.4 volt from emitter to base, that value being +0.4 volts for transistor 42. Thus transistor 40 will conduct when the voltage at its emitter and at junction 50 is about −0.4 volts, or in other words when the signal voltage on conductor 23 is about −2.2 volts. Similarly, transistor 42 will turn on and conduct when the voltage at its emitter and at junction 60 is about +0.4 volts, or when the voltage on conductor 23 is about +2.2 volts. It will be understood that the signal applied to the emitter of a transistor comprises the algebraic sum of any offset component and the instantaneous signal of interest, as scaled by divider 52, 54, 56 or 62, 64, 66.

The ±2.2 volt signal levels represent the positive and negative threshold levels and +Th and −Th illustrated in the lower two traces of FIG. 1. These thresholds are somewhat below the approximately 3 volt limit to a linear output from the amplifier 14 and serve to switch a respective transistor into conduction when exceeded. Considering for the moment only a positive signal which exceeds the +Th value, the voltage at junction 60 will be somewhat more positive than +0.4 such that the emitter to base voltage of transistor is more than +0.4 volts and it is turned on. Capacitor 46, having a typical value of 4.7 microfarad, is presumed to have been able to charge as the signal offset voltage increased to and beyond the threshold, the rate at which the signal offset exceeds the threshold being sufficiently slow and its duration or interval beyond the threshold sufficiently long that capacitor 46 has little effect on those dynamics. Accordingly, when the threshold is exceeded, transistor 42 begins to conduct sharply, resulting in the relatively rapid injection of current, represented by arrow 82, from the amplifier output, through resistor 66, to the integrator capacitor 29. This represents an increase in the feedback frequency response capability such that the offset signal is moved relatively rapidly back toward a neutral base line position. Transistor 40 responds in a similar manner to a signal exceeding the opposite threshold; however, the current flow is then from capacitor 29 through resistor 56 to the amplifier output as represented by arrow 80, such that the offset correction is in the opposite direction.

In keeping with a principal aspect of the invention, base emitter capacitor 46 is sufficiently large that a relatively higher frequency, and thus brief interval, signal which exceeds the threshold amplitude ±Th will not operate to apply a turn-on potential -cross the base-emitter junction of the transistor. For turn-on, the capacitor must charge up to at least 0.4-0.5 volts in the forward direction, yet a pacer pulse PP has such a short duration or interval (about 2 milliseconds) that the respective capacitor does not receive sufficient charge before the pulse ends. This is also true for large QRS complexes and the like which exceed the threshold for an interval less than about 30 milliseconds. The present embodiment requires that the signal go from near zero to its 3 volt limit and remain there for longer than 15 milliseconds in order for either capacitor 44 or 46 to acquire sufficient charge to turn on its respective transistor. In other words, more than about 2 microcoulombs of charge must be applied to this capacitor to initiate conduction.

In the event of a large QRS complex, which may exceed + or −Th but not reach the 3 volt limit, a somewhat longer interval, i.e., more than 30-40 milliseconds, is required to sufficiently charge the capacitor 44, 46. Therefore, the fast-recovery circuit is operative to ignore large amplitude ECG (QRS) signals as well as pacer pulses.

It will be appreciated that the interval required to charge capacitor 44 or 46 to the "transistor triggering" level will vary not only with the amplitude by which the excursion exceeds a threshold, but also with the charge on the capacitor. If the average or base line was shifted toward one of the + or − thresholds, the system would ignore even slightly lower frequency (longer interval) excursions if they exceeded the opposite threshold, and would ignore only slightly higher frequency (shorter interval) excursions if they exceeded the proximate threshold. However, an interval range less than about 2-30 milliseconds should ignore all pacer pulses and substantially all QRS peaks, while adequately responding to the very low frequencies (below 5 Hz) of any offset signals.

In the foregoing manner the capacitors 44, 46 act to bypass or ignore threshold-exceeding signals of relatively short duration. Although a pacer pulse PP will be clipped when it reaches the 3 volt limit of the amplifier, the fact that transistors 40, 42 did not conduct and thereby quickly alter the output of the integrator ensures that, when the pulse terminates, the amplifier output will immediately return substantially to the previous base line, as illustrated in the lowermost trace in FIG. 1.

According to another aspect of the invention, diodes 54, 64 are employed in the respective bias-establishing circuits for transistors 40, 42 to compensate for the temperature-dependent conduction characteristics of the base-emitter junctions of the transistors. The conduction characteristics of a typical diode may change by 2 millivolts per degree Centigrade, such that the turn-on bias level may change significantly for a wide excursion of temperatures. This would in turn appear to cause an undesirable shift in the threshold value at which the signal turns the transistor on. However, any such shift is minimized or eliminated by the fact that the diode 54 or 64 similarly shifts its characteristics as a function of the temperature.

The invention may be embodied in other specific forms without departing from the spirit or essential characteristics thereof. The present embodiments are, therefore, to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. An improved fast-recovery circuit connected in the output of a physiological waveform amplifier to a feedback circuit connected to the amplifier input, the feedback circuit including an integrator having resistance and capacitance means for normally supplying low frequency feedback to the amplifier input to cancel low frequency offset appearing thereat, and the fast-recovery circuit including threshold means connected in parallel with at least a substantial portion of said integrator resistance means and normally having a relatively high impedance, the impedance of said threshold means being substantially lowered at least for amplifier output signals in a very low frequency range of concern and greater than a characteristic amplitude threshold level to thereby increase the feedback frequency response of said integrator, the improvement wherein said threshold means includes: means for preventing response thereof to excursions in the amplifier output signal which are above said very low frequency range of concern and which exceed said amplitude threshold.

2. The improved fast-recovery circuit of claim 1 wherein signal excursions exceeding said threshold level and having a frequency characteristic greater than about 5 Hz are inoperative to change the frequency response of said integrator.

3. The improved fast-recovery circuit of claim 1 wherein said response preventing means operate to prevent response of said threshold means only when the amplifier output signal exceeds said amplitude threshold for less than about 30 milliseconds.

4. The improved fast-recovery circuit of claim 1 wherein said threshold means includes bias means having said output signal applied thereto and bias-responsive switch means, said switch means being nonconductive when the bias is less than a certain level and conductive when the bias is greater than said certain level, said threshold amplitude of said signal normally providing said certain bias level, and said responsive preventing means comprises other capacitance means valued and connected to substantially bypass signal excursions above said very low frequency range of concern without exceeding said certain bias level.

5. The improved fast-recovery circuit of claim 4 wherein said switch means comprises a pair of complementary semiconductors, each having at least two electrodes, and said other capacitance means comprises a respective pair of other capacitors each connected between a said electrode of a respective semiconductor and a common potential.

6. The improved fast-recovery circuit of claim 5 wherein said semiconductors are respective transistors each having base, emitter and collector electrodes, said bias voltage being measured from a respective said base to a respective said emitter, and each respective said other capacitor being connected across respective emitter and base electrodes.

7. The improved fast-recovery circuit of claim 6 wherein said bias means comprises a tapped resistive voltage divider, one end of said divider being for connection to a supply potential and the other end being connected to said amplifier output, said tap being connected to the emitter of said transistor and the bias voltage appearing thereat.

8. The improved fast-recovery circuit of claim 7 wherein said voltage divider includes a diode intermediate said tap and said supply potential, said diode being selected and poled to compensate for the temperature dependence of the base-emitter circuit of said transistor thereby to maintain substantially constant the amplitude of said amplifier output signal at which said certain biasing occurs.

* * * * *

UNITED STATES PATENT AND TRADEMARK OFFICE
CERTIFICATE OF CORRECTION

PATENT NO. : 4,147,990
DATED : April 3, 1979
INVENTOR(S) : Edwin A. Dokus and Thomas K. Naylor It is certified that error appears in the above-identified patent and that said Letters Patent are hereby corrected as shown below:

In column 2, line 26, delete "circuit" and insert --circuitry--;

In column 8, line 16, delete "responsive" and insert --response--.

Signed and Sealed this

Eleventh Day of September 1979

[SEAL]

Attest:

Attesting Officer

LUTRELLE F. PARKER
Acting Commissioner of Patents and Trademarks